United States Patent
Vivien et al.

(10) Patent No.: US 10,835,679 B2
(45) Date of Patent: Nov. 17, 2020

(54) NEEDLELESS INJECTION DEVICE EQUIPPED WITH AN IMPROVED PERCUSSION DEVICE

(71) Applicants: Gilles Vivien, Malakof (FR); Xavier Vigot, Veronnes (FR)

(72) Inventors: Gilles Vivien, Malakof (FR); Xavier Vigot, Veronnes (FR)

(73) Assignee: CROSSJECT, Dijon (FR)

( * ) Notice: Subject to any disclaimer, the term of this patent is extended or adjusted under 35 U.S.C. 154(b) by 364 days.

(21) Appl. No.: 15/848,050

(22) Filed: Dec. 20, 2017

(65) Prior Publication Data

US 2018/0117254 A1    May 3, 2018

Related U.S. Application Data

(63) Continuation of application No. PCT/FR2016/051655, filed on Jun. 30, 2016.

(30) Foreign Application Priority Data

Jun. 30, 2015 (FR) ...................... 15 56159

(51) Int. Cl.
- *A61M 5/30* (2006.01)
- *A61M 5/20* (2006.01)
- *A61M 5/315* (2006.01)

(52) U.S. Cl.
CPC ............ *A61M 5/3007* (2013.01); *A61M 5/20* (2013.01); *A61M 5/2046* (2013.01); *A61M 5/30* (2013.01);
(Continued)

(58) Field of Classification Search
CPC .... A61M 5/30; A61M 5/3007; A61M 5/3015; A61M 2005/3022; A61M 2005/2013;
(Continued)

(56) References Cited

U.S. PATENT DOCUMENTS

| 6,964,650 B2 * | 11/2005 | Alexandre | A61M 5/30 604/70 |
| 2003/0097093 A1 * | 5/2003 | Navelier | A61M 5/30 604/68 |

(Continued)

FOREIGN PATENT DOCUMENTS

| DE | 102007031714 | 1/2009 |
| FR | 2815544 | 4/2002 |

OTHER PUBLICATIONS

International Search Report for International Application PCT/FR2016/051655, dated Oct. 14, 2016.

*Primary Examiner* — Kami A Bosworth
*Assistant Examiner* — Leah J Swanson
(74) *Attorney, Agent, or Firm* — Burris Law, PLLC

(57) ABSTRACT

A needleless injector includes a cap, an injection system, a body, a gas generator, and a percussion device. The body is covered by the cap and is mounted to slide relative to the cap. The percussion device includes a striker that is slidingly mounted along a sliding axis between a rest position and a percussion position and a lock mechanism. The lock mechanism includes a lug and a retention tab. The lug projects from a peripheral face of the striker along an axis that is perpendicular to the sliding axis and has a first support ramp. The retention tab is attached to the cap, and has a second support ramp. The ramps are configured to move the retention tab radially when pushed by the striker from a retaining position to a release position and the retention tab is moved aside to release the striker.

11 Claims, 3 Drawing Sheets

(52) U.S. Cl.
CPC .... *A61M 5/31511* (2013.01); *A61M 5/31563* (2013.01); *A61M 2005/2013* (2013.01); *A61M 2005/2073* (2013.01)

(58) Field of Classification Search
CPC .......... A61M 2005/2073; A61M 5/155; A61M 5/2046; A61M 5/31511; A61M 5/31563; A61M 2005/208
See application file for complete search history.

(56) References Cited

U.S. PATENT DOCUMENTS

2007/0055214 A1* 3/2007 Gilbert .................... A61M 5/30
604/500
2013/0237921 A1 9/2013 Lannan et al.

* cited by examiner

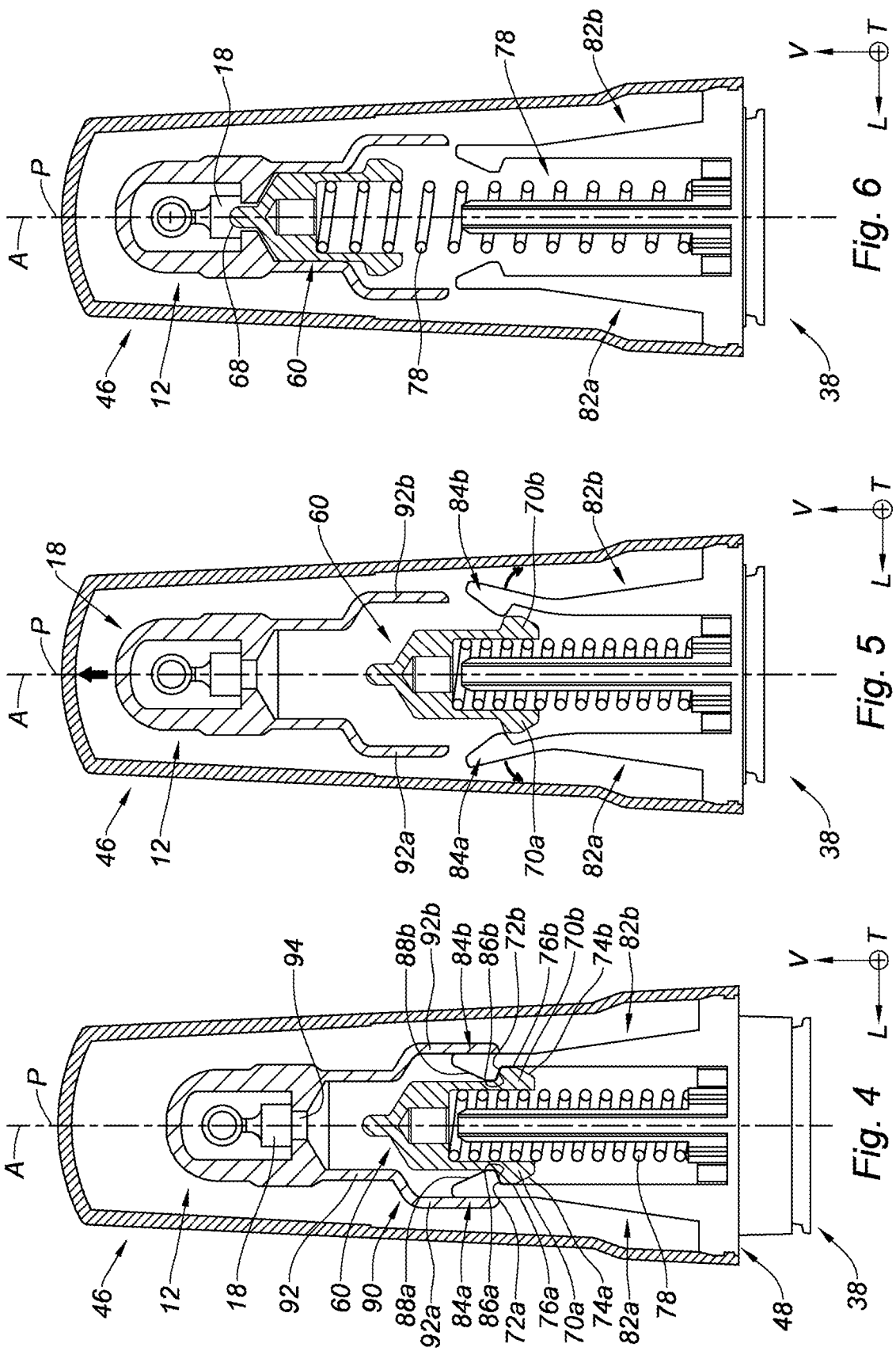

NEEDLELESS INJECTION DEVICE EQUIPPED WITH AN IMPROVED PERCUSSION DEVICE

CROSS-REFERENCE TO RELATED APPLICATIONS

This application is a continuation of International Application No. PCT/FR2016/051655, filed on Jun. 30, 2016, that claims priority to and the benefit of FR 15/56159 filed on Jun. 30, 2015. The disclosures of the above applications are incorporated herein by reference.

FIELD

The present disclosure relates to a needleless injection device equipped with a percussion device of a gas generator.

BACKGROUND

The statements in this section merely provide background information related to the present disclosure and may not constitute prior art.

The technical field of the present disclosure is one of disposable pre-filled needleless injection devices, operating with an energy source, for example, a gas generator, and used for intradermal, subcutaneous and intramuscular injections, of a liquid active ingredient for a therapeutic use in human or veterinary medicine.

The active ingredient is formed of a liquid more or less viscous, a liquid mixture, or a gel. The active ingredient may also be a solid dissolved in a solvent suitable for the injection or it may be formed by a pulverulent solid suspended at a certain concentration in a suitable liquid. The grain size distribution of the active ingredient must then be compatible with the diameter of the ducts in order to inhibit obstructing them.

Generally, an injection device includes, for example, as in the patent application FR-A-2815544 (equivalent to WO 02/34317), a body comprising successively a gas generator, an expansion chamber, a reservoir containing the liquid active ingredient and an injection system.

The reservoir is formed by a glass tube that is inserted into the body of the device and that is obstructed by an upstream plunger stopper and a downstream plunger stopper between that the liquid active ingredient is contained.

The downstream free end of the reservoir cooperates (i.e., interfaces) with an injection nozzle that defines at least one injection channel extending axially along an injection axis.

In addition, the injection device includes a hollow cover that envelops the body and that defines a lower opening adapted for the passage of the injection nozzle.

The free end of the injection nozzle that protrudes out of the body and of the cover is protected by a removable cap and a stopper that houses the cap.

In order to enable the injection of the active ingredient, the body is slidably mounted in the cover, from bottom to top along a sliding axis, between a rest position and an injection position, the driving of the body being achieved when the patient presses the injection nozzle on his skin.

The displacement of the body in the cover enables the triggering of the gas generator generating a pressurized gas that drives the plunger stoppers in displacement in order to inject the active ingredient through the patient's skin via the injection nozzle.

To this end, the injection device is equipped with a percussion device that includes a striker slidably mounted along a sliding axis, between a rest position in that the striker is blocked in translation by a lock mechanism against a prestressed spring, and a percussion position in that the striker is released by the lock mechanism to strike a primer of the gas generator under the action of the spring.

The document FR-A-2815544 describes a lock mechanism that includes two projections that extend radially from the peripheral face of the striker and each having a helical-type ramp.

In addition, the cover has two lugs each having a helical-type ramp, the ramps of the cover being adapted to bear on the associated ramps of the striker.

The ramps are designed to enable, by friction, the driving of the striker according to a combined translational and pivotal movement about the sliding axis, when the body is driven towards its injection position.

The pivoting of the striker allows the striker to be released from an obstruction that opposes its axial sliding, against the prestressed spring.

Once released from its obstruction, the striker is forcibly driven towards its percussion position, by the prestressed spring provided for this purpose, to strike the primer of the gas generator and trigger the gas generator.

A drawback of this type of percussion device is the considerable friction of the striker on the associated ramps of the cover that results in an energy loss and that may sometimes result in a blocking of the device.

In addition, the radial forces exerted on the retaining tabs by the striker can cause plastic deformations if the pushing force induced by the spring is too high.

SUMMARY

The present disclosure aims in particular at overcoming these and other drawbacks by providing a percussion device more reliable and limiting the frictions.

For this purpose, the present disclosure relates to a needleless injection device including a cover, an injection system, a body, a gas generator, and a percussion device. The injection system includes at least one plunger, a reservoir containing an active ingredient, and an injection nozzle defining at least one injection channel. The body is enveloped by the cover and is slidably mounted relative to the cover, from bottom to top along a sliding axis, between a rest position and an injection position. The gas generator comprises a primer. The percussion device includes a striker slidably mounted along the sliding axis between a rest position, in that the striker is blocked in translation by a lock mechanism against a prestressed spring, and a percussion position, in that the striker is released by the lock mechanism to strike the primer of the gas generator under the action of the spring. The lock mechanism of the striker includes a lug, a retaining tab, and an obstruction. The lug protrudes from a peripheral face of the striker along an axis generally perpendicular to the sliding axis and has a first bearing ramp. The retaining tab is secured to the cover and has a second bearing ramp arranged facing the first bearing ramp. The ramps are configured to cooperate together in order to drive the retaining tab radially under the effect of the push of the striker, from a retaining position in that the first ramp bears axially on the second ramp so that the retaining tab opposes the sliding of the striker, to a release position in that the retaining tab is spaced apart in order to release the striker. The obstruction is secured to the body and is configured to constrain the retaining tab in its retaining position, when the body occupies its rest position, and to release the retaining tab in its release position when the body occupies its injection position.

In one form, the present disclosure may allow limiting the movement of the striker to a linear displacement in order to reduce the frictions between the striker and the retaining tab.

In another form, each of the first ramp and the second ramp extends radially by having a downward inclination that is adapted to enable the second ramp of the retaining tab to slip on the first ramp of the lug and to space the retaining tab apart towards its release position, under the effect of the axial push of the striker driven by the associated spring.

In yet another form, the lug of the striker has a first counter-ramp and the retaining tab has a second counter-ramp. The counter-ramps extends radially by having an upward inclination that is adapted to enable the second counter-ramp of the retaining tab to slip on the first counter-ramp of the lug and to drive the retaining tab towards its release position, when the striker is slidably driven from its rest position, to its percussion position.

According to another aspect of the present disclosure, the cover includes a soleplate, forming a cover bottom, that extends perpendicular to the sliding axis, and the retaining tab extends axially along the sliding axis from a base linked on the soleplate, to a head that defines the second ramp, the retaining tab being elastically deformable radially to enable the spacing of the tab from its retaining position to its release position.

In another form, the prestressed spring that cooperates with the striker is axially interposed, along the sliding axis, between the soleplate of the cover and a bearing face of the striker.

In one form, the retaining tab is made of a plastic material integral with the soleplate of the cover.

In another form, the body defines a guide sheath of the striker, and the body has a generally tubular shape along the sliding axis and is configured to axially guide the striker between its rest position and its percussion position.

In yet another form, the guide sheath defines at least one axial groove that forms the obstruction of the retaining tab and that is adapted to form a radial bearing of an axial free end of the retaining tab.

In one form, an axial free end of the striker forms a stud adapted to strike and ignite the primer of the gas generator.

In another form, the percussion device has a symmetric design relative to an axial plane passing through the sliding axis, the device including, by symmetry, two retaining tabs forming a clamp each interfacing with an associated lug of the striker.

According to another form, the active ingredient contained in the reservoir is selected from the group consisting of: Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparioid sodium, Enoxaparin sodium, Estradiol cypionate, Medroxyprogesterone acetate, Nadroparin calcium, Methylprednisolone acetate, Heparin calcium, Terbutaline.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in that:

FIGS. 4, 5 and 6 are schematic axial cross-sectional views, that illustrate the successive steps of the triggering of the percussion device.

Figure 1:
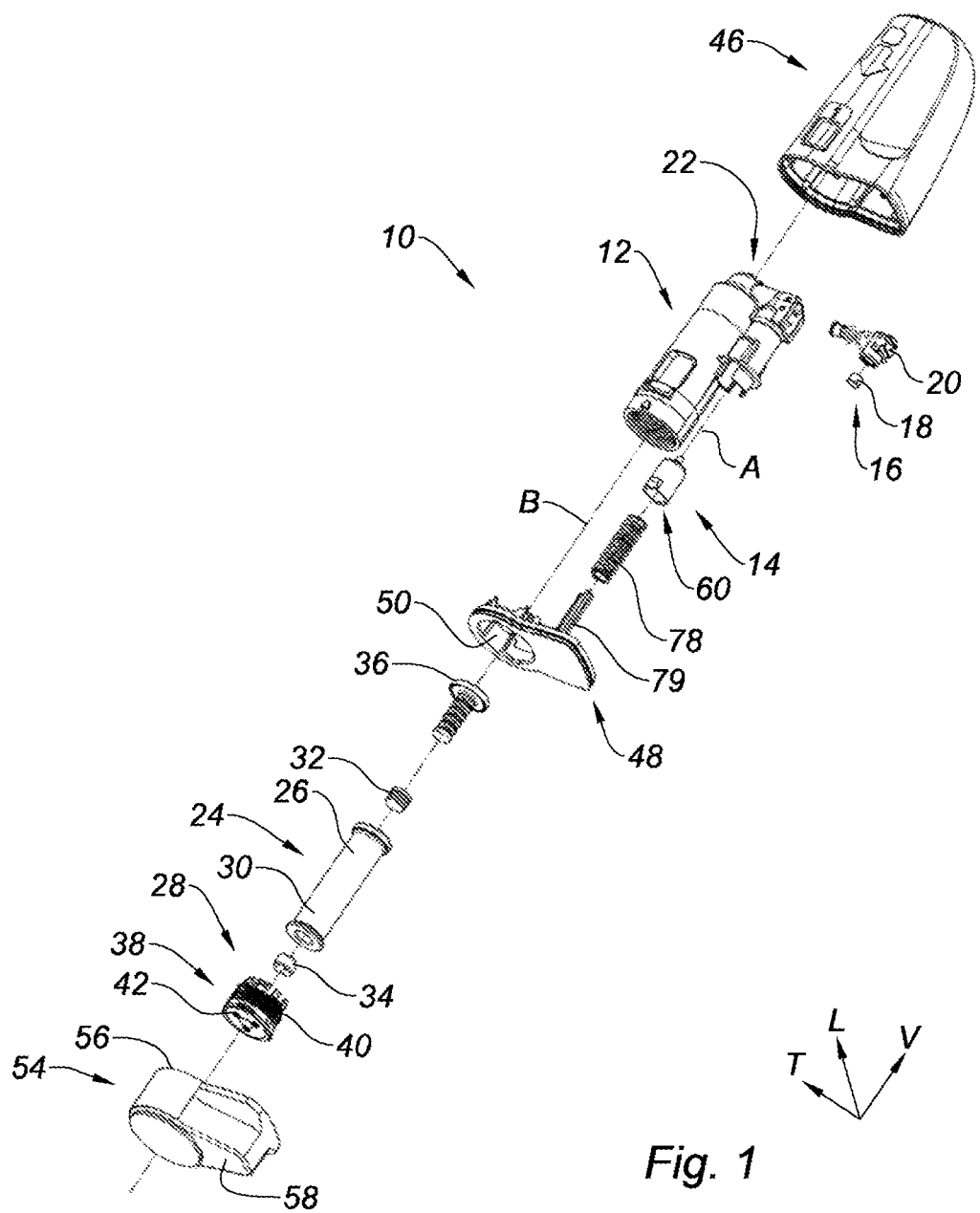
FIG. 1 is an axially exploded perspective view, that illustrates a needleless injection device including a percussion device, according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the description and the claims, in order to clarify the description and the claims, the terminology longitudinal, vertical and transverse will be adopted without limitation with reference to the trihedron L, V, T indicated in the figures.

In addition, in the present application, the terms "top", "bottom", "upper", "lower", "horizontal", "vertical" and their derivatives refer to the position or the orientation of an element or a component, this position or the orientation being considered with reference to the orientation of the device in the figures and to the trihedron L, V, T, without reference to the earth's gravity.

Similarly, the terms "axial" and "radial" should be understood with reference to the vertical sliding axis A of the body of the injection device.

Also, to facilitate the understanding of the description, identical and symmetrical elements with respect to the plane of symmetry P are indicated by the same reference numerals distinguished by the letter (a) or (b).

FIG. 1 shows a needleless injection device 10, or needleless syringe, that includes a U-shaped body 12 comprising successively a percussion device 14, a gas generator 16 comprising a primer 18 and a pyrotechnic charge 20, an expansion chamber 22, a reservoir 24 containing the liquid active ingredient 26 and an injection system 28.

The percussion device 14 and the gas generator 16 form a first linear sub-assembly of the body 12 that extends axially along a vertical sliding axis A, and the reservoir 24 containing the active ingredient 26 and the injection system 28 form a second linear sub-assembly of the body 12 that extends axially along a second vertical injection axis B.

According to one form, the body 12 is made of a plastic material.

These two sub-assemblies are linked to each other by the expansion chamber 22 that has an axis perpendicular to the axes A, B of the sub-assemblies.

The reservoir 24 is formed by a glass tube 30 obstructed by an upstream plunger stopper 32 and a downstream plunger stopper 34 between that the liquid active ingredient 26 is contained, the plunger stoppers being made of an elastically-deformable elastomer-based material.

The reservoir 24 is inserted into the body 12 and is blocked vertically at its upstream portion by a cylindrical part 36 provided with a central opening allowing to set the upstream plunger stopper 32 into communication with the expansion chamber 22 and at its downstream portion by an injection nozzle 38.

The nozzle 38 has a cylindrical shape along the injection axis B that is defined by a cylindrical peripheral face 40 provided with a thread, the thread being intended to cooperate (interface) with a complementary tapping formed on the inner wall of the downstream end of the body 12.

In addition, the nozzle 38 defines three axial injection channels 42 parallel to the injection axis B, illustrated in FIG. 1.

Figure 2:
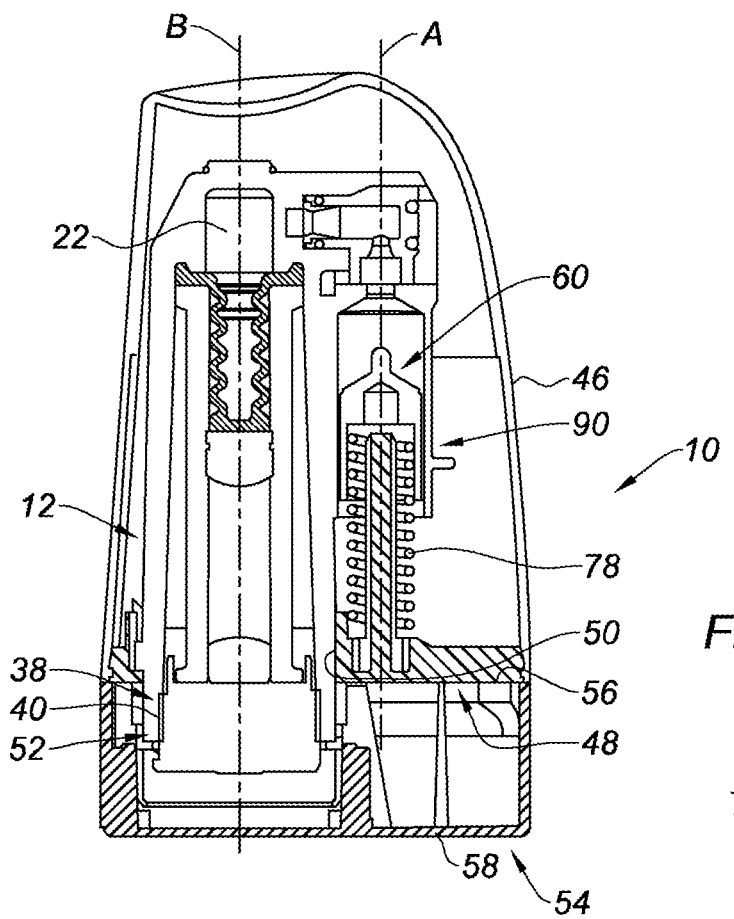
FIG. 2 is an axial cross-sectional view, that illustrates the striker of the percussion device of FIG. 1 slidably mounted in the body.

Referring to FIGS. 1 and 2, the body 12 is enveloped by a hollow cover 46 that defines a lower opening closed by a horizontal soleplate 48 forming a cover bottom.

The soleplate 48 defines a circular passage 50 about the injection axis B that is adapted for the passage of the injection nozzle 38 and of the downstream end of the body 12, so that the nozzle 38 includes a lower section 52 protruding vertically downwards out of the cover 46.

Also, the injection device 10 is equipped with a stopper 54 that is defined vertically by an open upper face 56 bearing on the soleplate 48 of the cover 46, and a generally flat closed lower face 58.

The stopper 54 is removably mounted on the body 12 by a bayonet-type lock mechanism.

According to another aspect, the percussion device 14 includes a striker 60 that has a generally cylindrical blind shape along the sliding axis A and that is defined by a cylindrical peripheral wall 62.

According to a preferred form, the striker 60 is made of a metallic material, for example an alloy known by the acronym, "ZAMAK".

The percussion device 14 has a symmetric design relative to a longitudinal axial plane of symmetry P, passing through the sliding axis A, illustrated in FIGS. 4 to 6.

Figure 3:
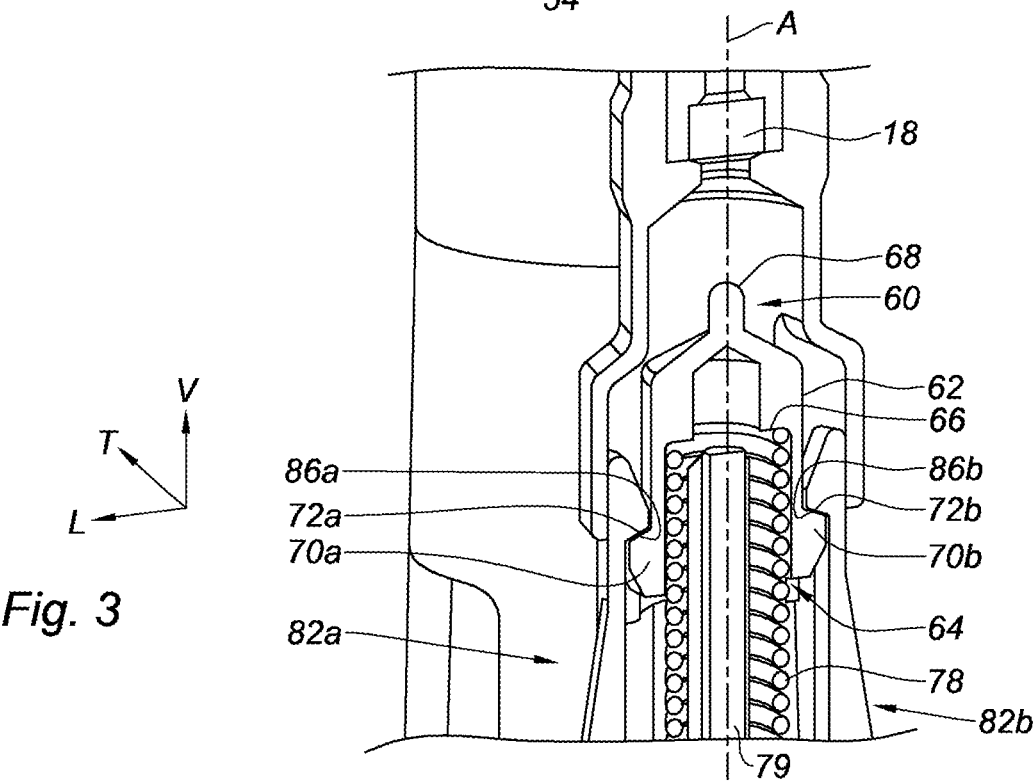
FIG. 3 is a detail perspective axial sectional view, that illustrates the striker and the retaining tabs of the device of FIG. 1.

As shown in FIG. 3, the striker 60 forms a blind inner housing 64 that opens axially at the lower free end of the striker 60 and that is defined by an upper annular seat 66.

In addition, the striker 60 has, at an upper axial free end, a stud 68 adapted to strike and ignite the primer 18 of the gas generator 16.

Also, the striker 60 is equipped with two symmetrical opposite lugs 70a, 70b that protrude radially from the peripheral face 62 of the striker 60 and each having a first upper bearing ramp 72a, 72b respectively.

Each of the first ramps 72a, 72b extends generally radially from the peripheral face 62 of the striker 60, by having a downward inclination. According to one form, the angle of inclination is about twenty degrees relative to a non-inclined horizontal radial plane.

Similarly, each of the lugs 70a, 70b of the striker 60 has a first lower counter-ramp 74a, 74b respectively, each extending generally radially from the peripheral face 62 of the striker 60, by having an upward inclination. According to one form, the angle of inclination is about sixty degrees relative to a non-inclined horizontal radial axis.

The first ramps 72a, 72b and the first counter-ramps 74a, 74b are linked to each other by an axial portion 76a, 76b respectively.

According to FIG. 4, the striker 60 cooperates with a prestressed helical spring 78 that is axially interposed, along the sliding axis A, between an upper face of the soleplate 48 of the cover 46 and the annular seat 66 of the striker 60.

The spring 78 is fitted on a mast 79 that extends axially from the soleplate 48 and that is designed to guide the spring 78 along the sliding axis A.

In addition, the spring 78 may be replaced by any other elastic return means, such as for example a gas spring.

Furthermore, the percussion device 14 includes two retaining tabs 82a, 82b, illustrated in FIG. 4, that are arranged on either side of the plane of symmetry P.

Each retaining tab 82a, 82b extends axially, along the sliding axis A, from a base linked on the soleplate 48 of the cover 46, to a head 84a, 84b respectively that forms a notch protruding radially towards the sliding axis A.

Each head 84a, 84b defines a second ramp 86a, 86b respectively, the second ramps 86a, 86b extending in front of and parallel to the first ramps 72a, 72b respectively of the striker 60.

Similarly, each head 84a, 84b defines a second counter-ramp 88a, 88b respectively, the second counter-ramps 88a, 88b extending parallel to the first counter-ramps 74a, 74b respectively of the striker 60.

According to a preferred form, each retaining tab 82a, 82b is made of a plastic material integral with the soleplate 48 of the cover 46.

As shown in FIG. 4, the body 12 defines a guide sheath 90 of the striker 60. The striker 60 has a generally tubular shape along the sliding axis A that is configured to axially guide the striker 60.

To this end, the sheath 90 has a cylindrical guide section 92 that is open axially downwards to enable the passage of the striker 60 and that defines an upper passage 94 for access to the primer 18 of the pyrotechnic charge 20.

In addition, the sheath 90 defines two symmetrical axial grooves forming an obstruction 92a, 92b respectively, that are designed to form a radial bearing of the heads 84a, 84b of the retaining tabs 82a, 82b respectively.

The assembly formed by the lugs 70a, 70b of the striker 60, the retaining tabs 82a, 82b and the obstructions 92a, 92b forms a lock mechanism of the striker 60.

In order to enable the triggering of the percussion device 14, several elements are movable, as it can be understood from reading the following description, with reference to FIGS. 4 to 6.

The body 12 is slidably mounted relative to the cover 46, from bottom to top along the sliding axis A, between a rest position, illustrated in FIG. 4, in that the percussion device 14 is not triggered, and an injection position, represented in FIG. 6, in that the body 12 is axially slid upwards and the percussion device 12 is triggered.

The injection nozzle 38 being secured to the body 12, the body 12 is driven towards its injection position when the patient applies the nozzle 38 on his skin and drives the cover 46 downwards, in the direction of his skin.

Also, the striker 60 is slidably mounted along the sliding axis A, between a rest position illustrated in FIG. 4, in that the striker 60 is blocked in translation by the lock mechanism against the prestressed spring 78, and a percussion position illustrated in FIG. 6, in that the striker 60 is released by the lock mechanism to strike the primer 18 of the gas generator 16 under the action of the spring 78.

Indeed, as shown in FIG. 4, the second bearing ramps 86a, 86b formed by the retaining tabs 82a, 82b bear axially on the first bearing ramps 72a, 72b formed by the lugs 70a, 70b of the striker 60 to oppose the axial sliding of the striker 60 upwards, against the spring 78.

Furthermore, the head 84a, 84b of each retaining tab 82a, 82b is radially blocked by the obstructions 92a, 92b provided for this purpose, to inhibit the spacing of the tabs 82a, 82b.

FIG. 5 illustrates an intermediate step of sliding the body 12, between its rest position and its injection position, during that step the obstructions 92a, 92b slide upwards and release the tabs 82a, 82b that space apart radially outwards under the effect of the axial bearing of the first ramps 72a, 72b of the striker 60 on the second ramps 86a, 86b of the tabs 82a, 82b.

Indeed, the inclination of the ramps 72a, 72b, 86a, 86b is adapted to make the retaining tabs 82a, 82b slip and space apart radially outwards.

For this purpose, it is understood that the retaining tabs 82a, 82b are elastically deformable radially between a retaining position illustrated in FIG. 4, and a release position illustrated in FIG. 5.

FIG. 6 illustrates the end of stroke of the striker 60 that occupies its percussion position in that the stud 68 strikes and ignites the primer 18 in order to trigger the gas generator 16 and the injection of the active ingredient.

Thus, the present disclosure allows limiting the frictional forces that oppose the sliding of the striker 60, in particular by reducing the movement of the striker 60 to a linear movement.

In addition, the friction surfaces defined by the first ramps 72a, 72b and the second ramps 86a, 86b are relatively small.

It is possible to reduce these friction surfaces by acting on the shapes of the ramps to limit the bearing of the ramps on each other to a linear bearing, for example by conferring a convex domed shape to the first ramps 72a, 72b and a flat shape to the associated second ramps 86a, 86b.

Similarly, the present disclosure avoids possible plastic deformations of the retaining tabs 82a, 82b when the striker 60 occupies its rest position, in that position the striker exerts a radial spacing force on the head of the retaining tabs 82a, 82b.

Indeed, the obstructions 92a, 92b bear radially along the entire length of the heads 84a, 84b respectively, thereby inhibiting the torsion of the heads 84a, 84b when the striker 60 occupies its rest position.

These characteristics allow making the body 12 in a plastic material, that allows a mass reduction in comparison with a body made of metal.

According to another aspect, the triggering device is adapted to promote the mounting of the striker 60 in its rest position, by the presence of the first counter-ramps 74a, 74b of the striker 60 and the second counter-ramps 88a, 88b of the retaining tabs 82a, 82b, that enable the spacing of the tabs 82a, 82b during the sliding of the striker 60 downwards from its percussion position to its rest position.

It should be also noted that once the percussion device has been triggered, it is no longer possible to reposition the striker in its original position in that it is retained by the retaining tabs 82a, 82b.

This provides that the injection device 10 could not be reused.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A needleless injection device including:
a cover;
an injection system that comprises at least one plunger, a reservoir containing an active ingredient, and an injection nozzle defining at least one injection channel;
a body that is enveloped by the cover and that is slidably mounted relative to the cover, from bottom to top along a sliding axis, between a rest position and an injection position;
a gas generator that comprises a primer; and
a percussion device that includes a striker and a lock mechanism, wherein:
the striker is slidably mounted along the sliding axis between a rest position, in that the striker is blocked in translation by the lock mechanism against a prestressed spring, and a percussion position, in that the striker is released by the lock mechanism to strike the primer of the gas generator by the action of the spring, and
the lock mechanism includes:
a lug that protrudes from a peripheral face of the striker along an axis perpendicular to the sliding axis and that has a first bearing ramp,
a retaining tab that is secured to the cover and that has a second bearing ramp arranged opposite to the first bearing ramp, the ramps being configured to interface with each other to drive the retaining tab radially under the effect of the push of the striker, from a retaining position in that the first ramp bears axially on the second ramp such that the retaining tab opposes the sliding of the striker, to a release position in that the retaining tab is spaced apart in order to release the striker, and
an obstruction that is secured to the body and that is designed to constrain the retaining tab in its retaining position, when the body is at the rest position, and to release the retaining tab in its release position when the body is at the injection position.

2. The needleless injection device according to claim 1, wherein each of the first bearing ramp and the second bearing ramp extends radially by having a downward inclination that is adapted to enable the second bearing ramp of the retaining tab to slip on the first bearing ramp of the lug and to space the retaining tab apart towards its release position, under the effect of the axial push of the striker driven by the prestressed spring.

3. The needleless injection device according to claim 1, wherein the lug of the striker has a first counter-ramp and the retaining tab has a second counter-ramp, each of the counter-ramps extends radially by having an upward inclination that is adapted to enable the second counter-ramp of the retaining tab to slip on the first counter-ramp of the lug and to drive the retaining tab towards its release position, when the striker is slidably driven from its rest position, to its percussion position.

4. The needleless injection device according to claim 1, wherein the cover includes a soleplate that forms a cover bottom and that extends perpendicular to the sliding axis, and the retaining tab extends axially along the sliding axis from a base linked on the soleplate to a head that defines the second bearing ramp, the retaining tab is radially elastically deformable to enable the spacing of the tab from its retaining position to its release position.

5. The needleless injection device according to claim 4, wherein the prestressed spring interfaces with the striker and is axially interposed along the sliding axis between the soleplate of the cover and a bearing face of the striker.

6. The needleless injection device according to claim 4, wherein the retaining tab is made of a plastic material integral with the soleplate of the cover.

7. The needleless injection device according to claim 1, wherein the body defines a guide sheath of the striker, the striker has a tubular shape along the sliding axis that is configured to axially guide the striker between its rest position and its percussion position.

8. The needleless injection device according to claim 7, wherein the guide sheath defines at least one axial groove that forms the obstruction of the retaining tab and that is adapted to form a radial bearing of an axial free end of the retaining tab.

9. The needleless injection device according to claim 1, wherein an axial free end of the striker forms a stud adapted to strike and ignite the primer of the gas generator.

10. The needleless injection device according to claim 1, wherein the percussion device has a symmetric design relative to an axial plane passing through the sliding axis, the device including, by symmetry, two retaining tabs forming a clamp each interfacing with an associated lug of the striker.

11. The needleless injection device according to claim 1, wherein the active ingredient contained in the reservoir is selected from the group consisting of: Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparoid sodium, Enoxaparin sodium, Estradiol cypionate, Medroxyprogesterone acetate, Nadroparin calcium, Methylprednisolone acetate, Heparin calcium, Terbutaline.

* * * * *